US00PP35681P2

(12) United States Plant Patent
Thompson et al.

(10) Patent No.: US PP35,681 P2
(45) Date of Patent: Mar. 12, 2024

(54) RASPBERRY PLANT NAMED 'HFG 1714'

(50) Latin Name: ***Rubus idaeus* L.**
Varietal Denomination: HFG 1714

(71) Applicant: Hortifrut Genetics Limited, Dublin (IE)

(72) Inventors: Ellen Thompson, Watsonville, CA (US); Max Laddon, Santa Cruz, CA (US)

(73) Assignee: Hortifrut Genetics Limited, Dublin (IE)

( * ) Notice: Subject to any disclaimer, the term of this patent is extended or adjusted under 35 U.S.C. 154(b) by 0 days.

(21) Appl. No.: 18/078,353

(22) Filed: Dec. 9, 2022

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 5/0887
See application file for complete search history.

*Primary Examiner* — Kent L Bell
(74) *Attorney, Agent, or Firm* — King IP Law; Joshua King

(57) ABSTRACT

A new and distinct cultivar of primocane-fruiting raspberry named 'HFG 1714'. The new variety reliably provides balanced heavy crop load on both primocanes and floricanes with very large, conical, extremely firm, subacid, pinkish-red colored berries suited for the fresh market. Plants possess high vigor, high number of spawn, and exceptional bud break in the floricane cycle.

6 Drawing Sheets

Latin name of the genus and species of the plant claimed: *Rubus idaeus* L.

Variety denomination: 'HFG 1714'.

BACKGROUND AND SUMMARY

The new primocane-fruiting raspberry cultivar designated as 'HFG 1714' is shown herein. Botanically known as *Rubus idaeus* L., the new variety 'HFG 1714' resulted from a hand-pollinated cross of female parent 'PBBrasp1348' (U.S. Plant Pat. No. 29,368P2), and the male parent '1338' (unpatented) both of which are genotypes from the same breeding program. Hand-pollination from this directed cross occurred in April 2015. Seeds from this population were harvested, cleaned, germinated, and subsequently established as seedlings in spring 2016 in Watsonville, California, Santa Cruz County, USA.

'HFG 1714' was first identified during the floricane-fruiting cycle on 31-May, 2017 in a substrate block where seedling populations had been planted into 10 L pots the prior spring. The selection ultimately identified as 'HFG 1714' was first propagated asexually by crown division (of that original potted 'HFG 1714' plant, which became the mother-plant for subsequent 'HFG 1714' plants) in December 2017 in Watsonville, California, Santa Cruz County, USA.

The crown on the original 'HFG 1714' plant was parted into basal cane pieces (approximately 15 cm long) with root attached, re-potted and placed inside of a screenhouse. The remaining roots were chilled for 4 weeks and planted inside into an onsite greenhouse to force etiolated shoots. Once rooted, individual etiolated shoots (propagules) were planted into a single 10-plant plot. Harvest and post-harvest data were collected from plots of 'HFG 1714' for two years, from 2018 through 2019.

In June 2019, actively growing shoots from the original mother-plant were harvested from inside the screenhouse and sent to Lafayette, OR, USA, where vegetative material was established in vitro for micropropagation. Tissue-cultured plantlets of 'HFG 1714' were tested in replicated blocks across diverse environments within North America for performance and genetic stability.

BRIEF SUMMARY OF THE INVENTION

The present cultivar, 'HFG 1714' offers several advantages over the existing cultivar and maternal parent, 'PBBrasp1348' (U.S. Plant Pat. No. 29,368P2). Particularly for fruit firmness, 'HFG 1714' is noteworthy for its extreme firmness and extended post-harvest shelf life, as compared to the softer fruit and shorter post-harvest shelf life of 'PBBrasp1348'. Unlike its maternal parent, 'HFG 1714' is mid-season, whereas 'PBBrasp1348' fruits earlier in the season. Like its parent 'PBBrasp1348', fruit color of 'HFG 1714' is non-darkening under post-harvest evaluations, maintaining a fresh appearance. 'HFG 1714' offers greater yields over 'PBBrasp1348'. The extreme firmness, long shelf life, and improved yields of 'HFG 1714' offer significant advantages to growers, who require high yielding cultivars that can maintain a fresh appearance many days post-harvest.

In contrast to the male parent 1338' (unpatented), 'HFG 1714' is significantly greater in average berry weight and yield. 'HFG 1714' maintains the reduced acidity and aromatics of its male parent '1338', yet offers a standard pink/red color common in fresh-market commodity raspberry than the less familiar yellow-peach colors of '1338'. 'HFG 1714' maintains the sensorial properties of male parent '1338' while improving the yield and average berry weight; these traits offer growers the ability to produce a large crop of berries of pink/red color, with a flavor that is highly desirable to consumers.

In contrast to the comparison cultivar 'PBBrasp1381' (U.S. Plant Pat. No. 29,369) 'HFG 1714' has a non-darkening pinkish-red color after 7 days in cold storage (2° C.), whereas 'PBBrasp1381' darkens significantly to a medium red color. 'HFG 1714' possesses a similar berry weight, firmness and extended shelf life associated with 'PBBrasp1381'. 'HFG 1714' has reduced acidity and increased sugar content in comparison to 'PBBrasp1381'. These characteristics offer an improved flavor in comparison to the comparison cultivar.

Thus, these characteristics help define 'HFG 1714' as a new and distinct cultivar of primocane-fruiting raspberry. 'HFG 1714' may be recognized by its large non-darkening, pinkish-red berries, high yield, reduced acidity, aromatic flavor, extreme firmness, and shelf life.

BRIEF DESCRIPTION OF THE PHOTOGRAPHS

DETAILED DESCRIPTION

Figure 1:
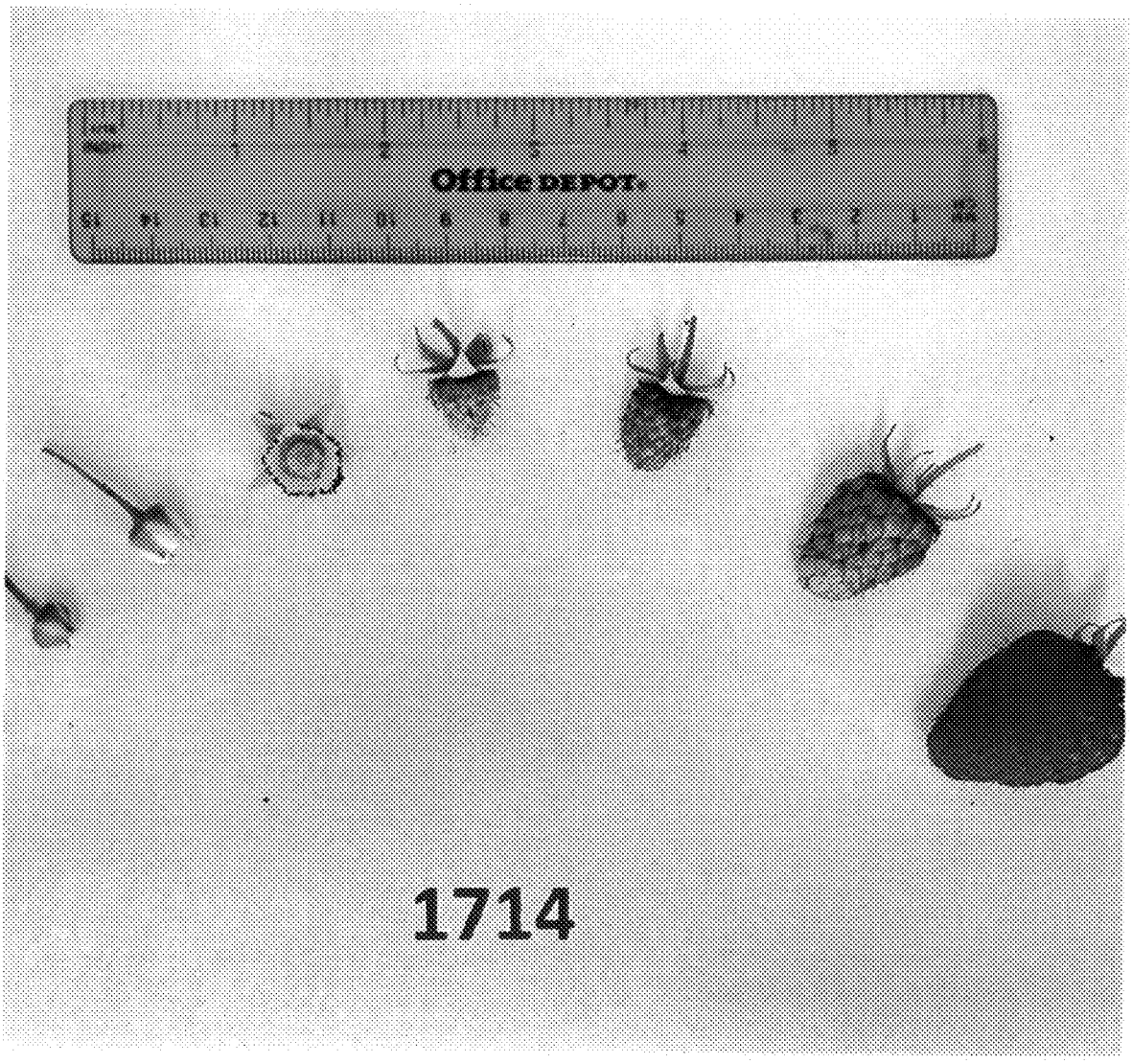
FIG. 1 is a photograph showing the progression of floral bud, flower, green and ripe fruit development of cultivar 'HFG 1714'.
Figure 2:
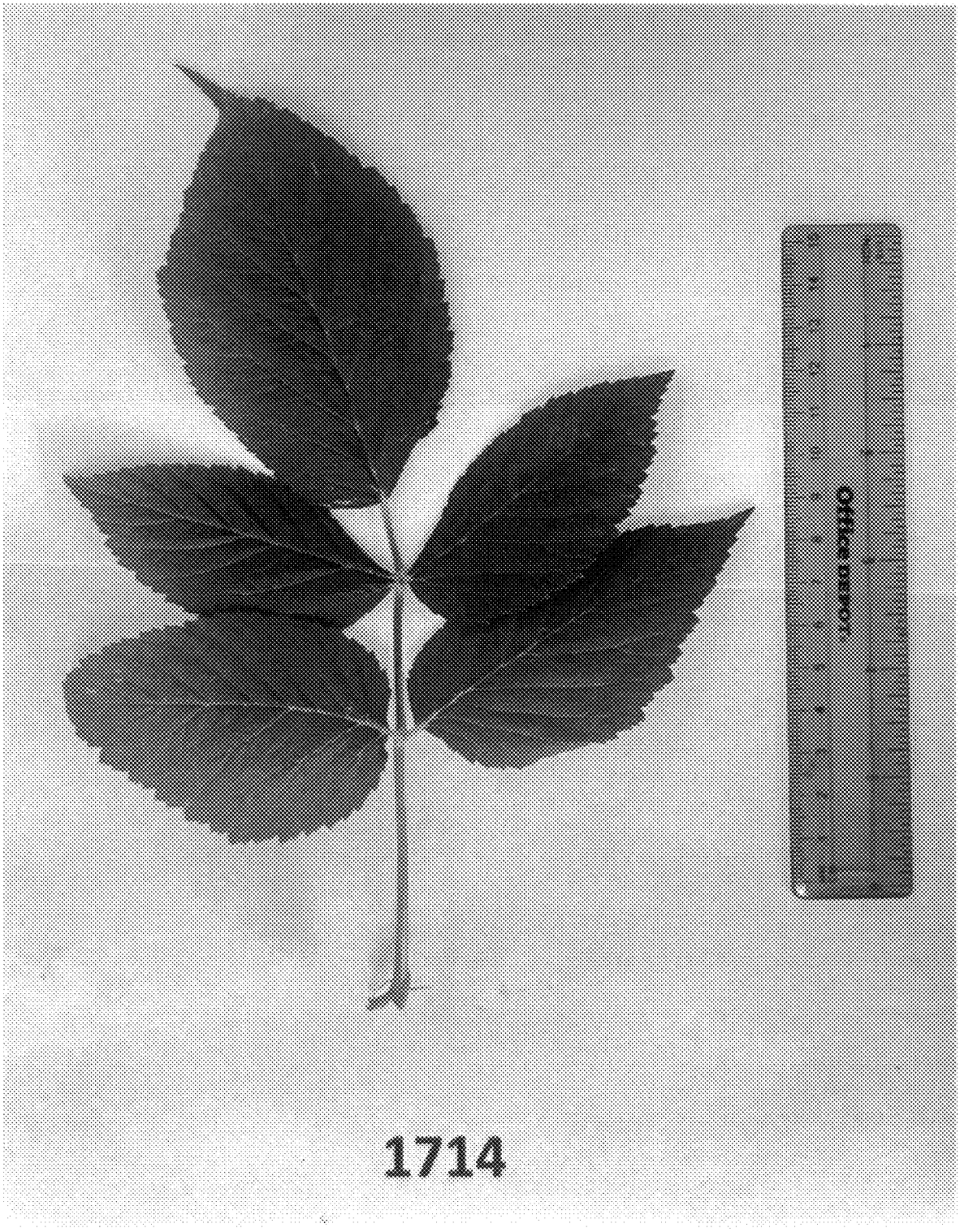
FIG. 2 is a photograph displaying the front side of a pentafoliate leaf of 'HFG 1714'.
Figure 3:
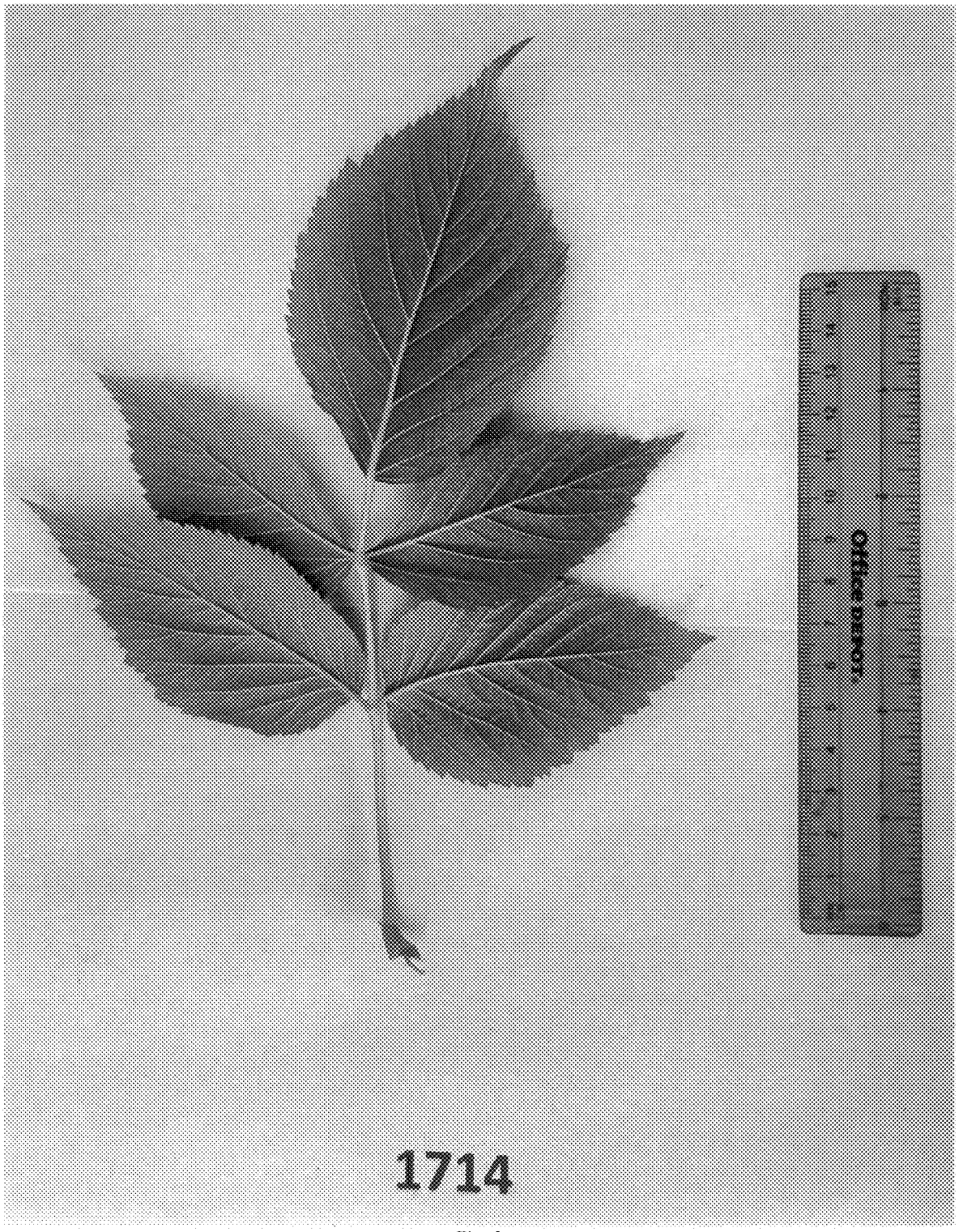
FIG. 3 is a photograph displaying the back side of a pentafoliate leaf of 'HFG 1714'.
Figure 4:
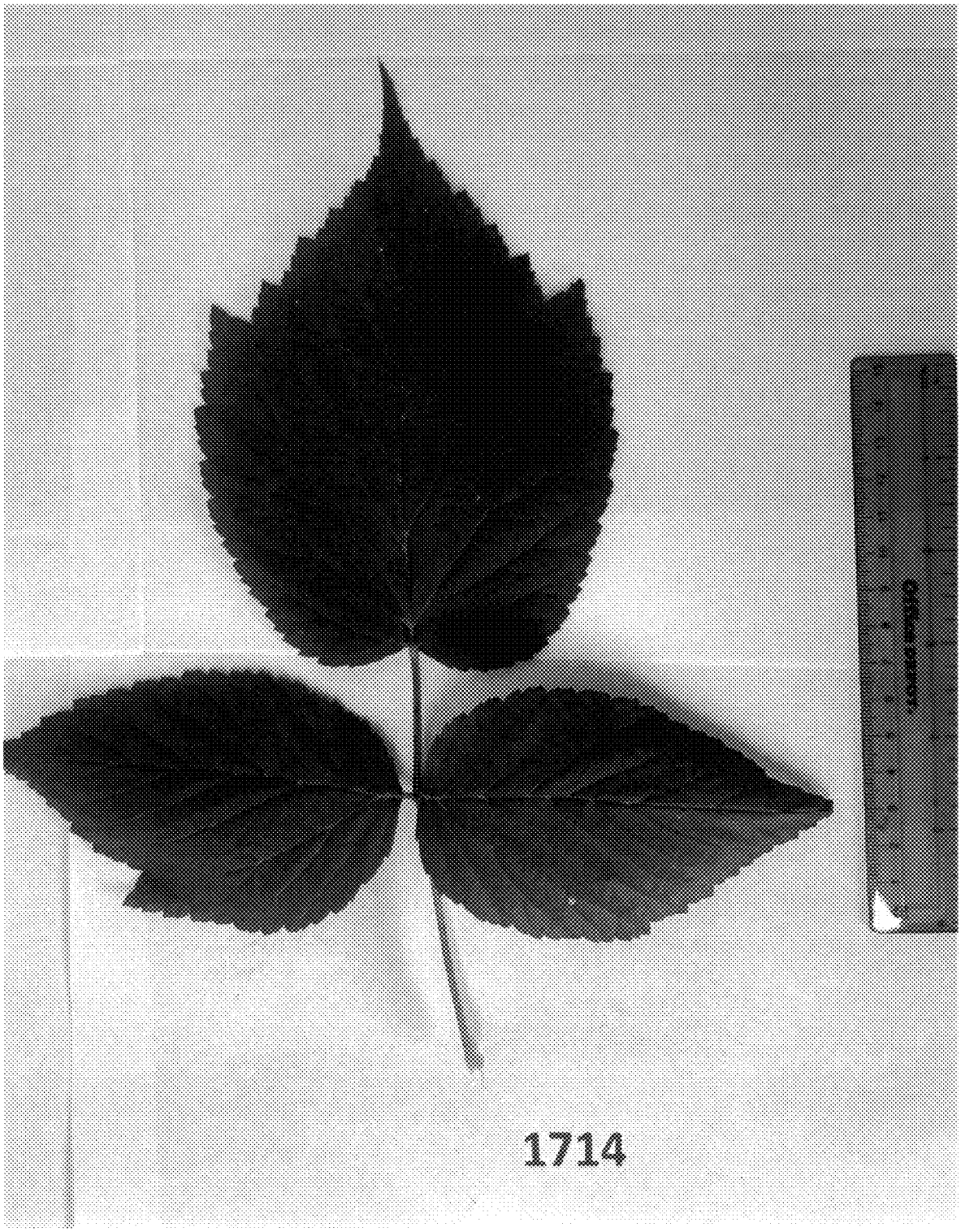
FIG. 4 is a photograph showing the front side of a trifoliate leaf of 'HFG 1714'.
Figure 5:
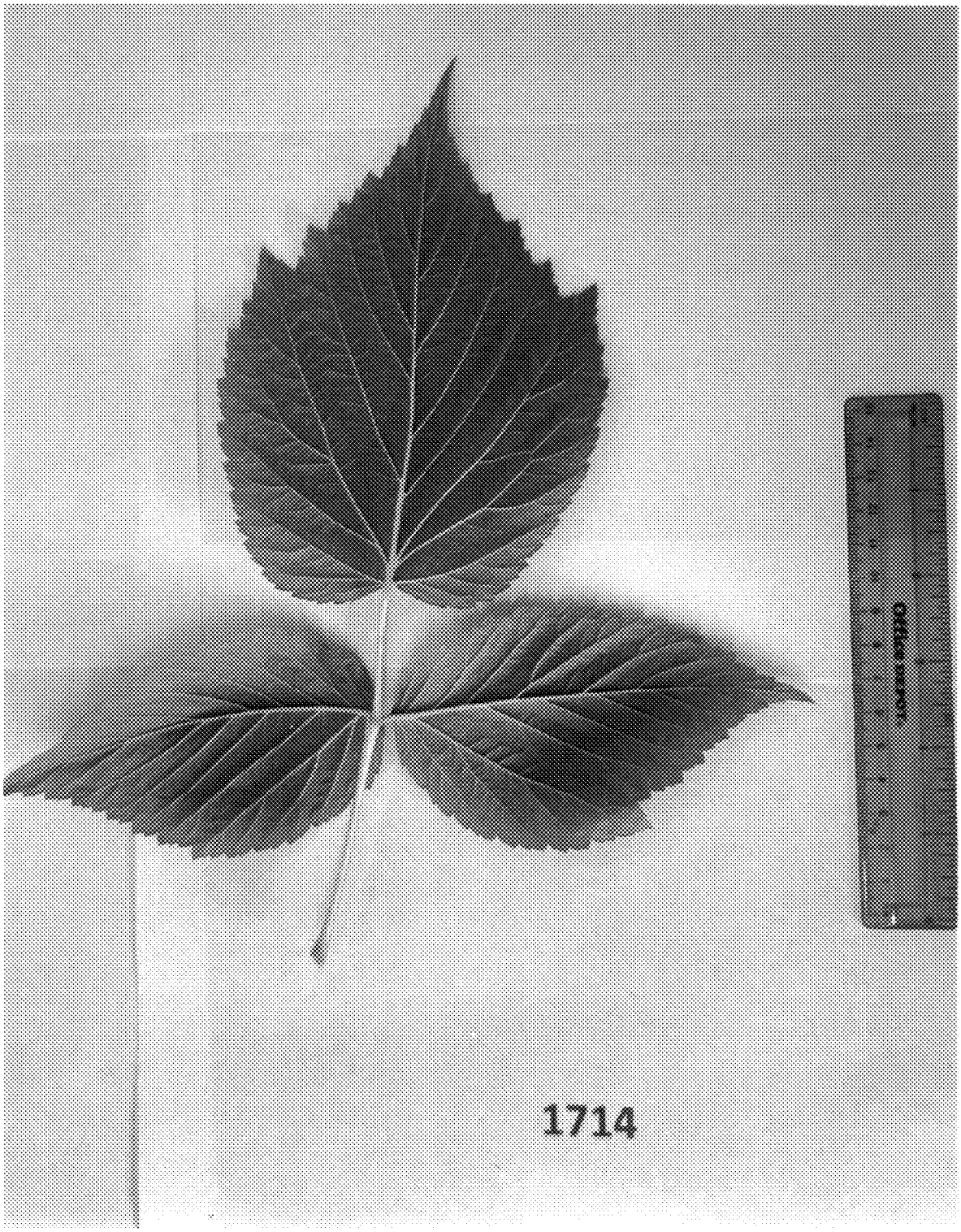
FIG. 5 is a photograph showing the back side of a trifoliate leaf of 'HFG 1714'.
Figure 6:
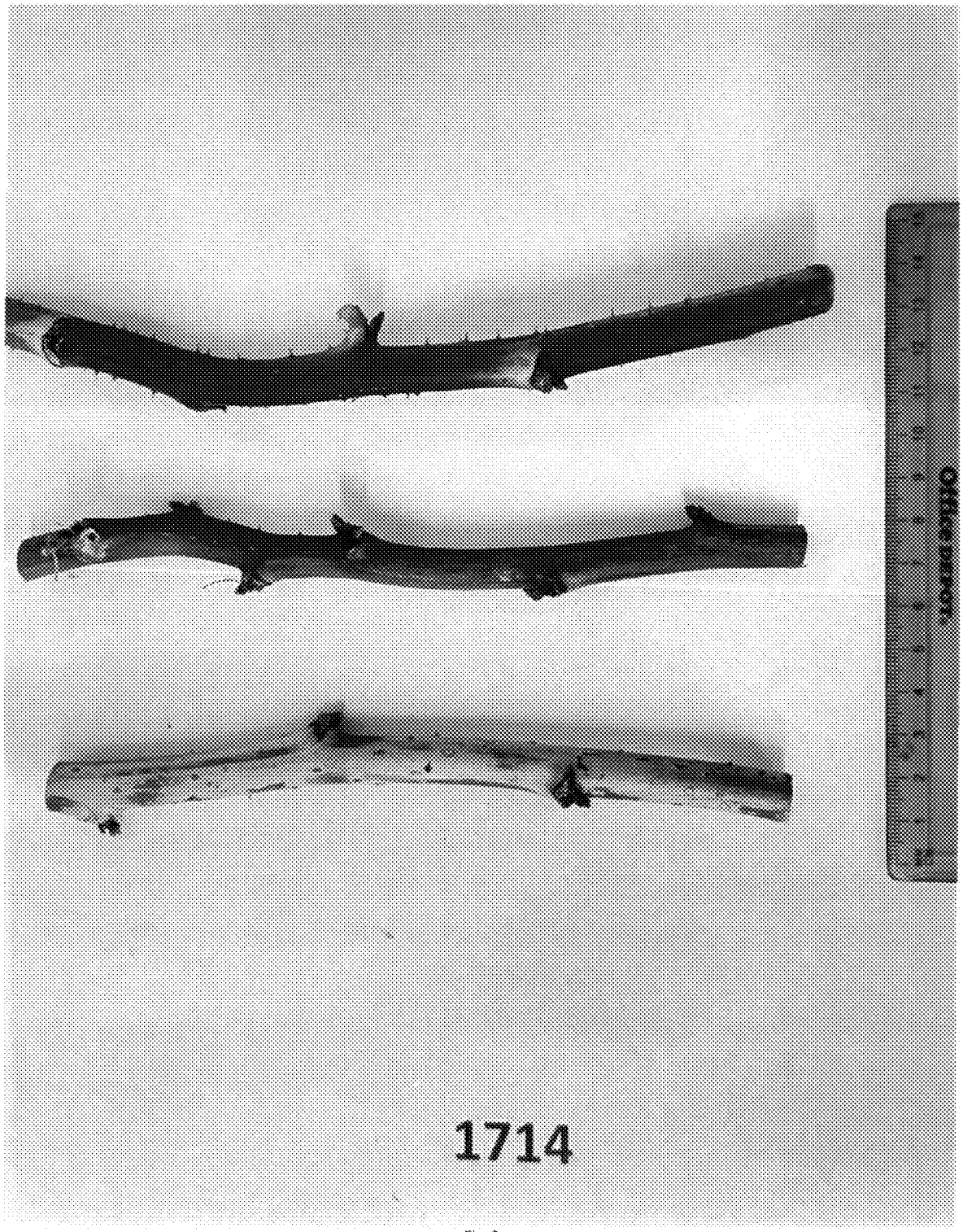
FIG. 6 is a photograph demonstrating basal, middle and apical cane colors of 'HFG 1714'.

Note: statements of characteristics herein represent exemplary observations of the cultivar herein and will vary depending on time of year, location, annual weather, etc.

Cultivar name: 'HFG 1714'.

Classification:

*Family*.—Rosaceae.

*Botanical name*.—*Rubus idaeus* L.

*Common name*.—Raspberry.

*Parentage*.—Female parent: 'PBBrasp1348'. Male parent: '1338'.

Growing location for the observations herein: Watsonville, California, USA.

Time of year (season): June 2022 for floricanes, and November 2022 for primocanes.

Age of plants used for this discussion: Crown age of about 1.5 years; floricane age 13 months; primocane age 8 months.

Age of plants used for the photographs in the figures: Primocane age 8 months.

Type of greenhouse covering or growing structure, or field: High tunnel over substrate-grown plants.

Light: Natural.

Color terminology refers to The R.H.S. Colour Chart, Royal Horticultural Society, Fifth Edition, London, United Kingdom (2007).

Observations for floricanes herein were made in June 2022. Observations for primocanes herein were made in November 2022.

Plant:

*Form/shape*.—Vase.

*Growth habit*.—Erect.

*Height*.—127 cm, as measured from cane base to apex.

*Spread*.—86.4 cm.

*Propagation methods*.—Tissue culture.

*Time to initiate and develop roots*.—26 days.

*Root description*.—Fibrous.

Primocanes:

*Cane diameter*.—Base: 1.2 cm | Middle: 1.0 cm | Tip: 0.3 cm.

*Cane length*.—2.0 m.

*Number of nodes per cane*.—47.

*Internode length*.—Base: 3.5 cm | Middle: 4.9 cm | Tip: 1.6 cm.

*Number of canes/hill*.—6.

*Cane color*.—Base — RHS 184D | Middle — RHS 175C | Tip — RHS 145D.

*Spines*.—Present.

*Spine density*.—Base: 7.0/cm$^2$ | Middle: 3.3/cm$^2$ | Tip: 4.5/cm$^2$.

*Spine shape*.—Acuminate.

*Spine length*.—0.26 cm.

*Spine width*.—0.16 cm.

*Spine apex descriptor*.—Acuminate.

*Spine color*.—RHS 150D.

*Vegetative bud shape*.—Acuminate.

*Vegetative bud length*.—0.6 cm.

*Vegetative bud diameter* (*base*).—0.5 cm.

*Vegetative bud diameter* (*tip*).—0.15 cm.

*Vegetative bud color*.—RHS 144C.

Floricanes:

*Cane diameter*.—Base — 1.2 cm | Middle — 1.0 cm | Tip — 0.9 cm.

*Cane length*.—91.4 cm.

*Number of nodes per cane*.—16. Internode Length: Base — 5.5 cm | Middle — 7.5 cm | Tip — 3.7 cm.

*Cane color*.—Lower Cane — RHS 164A | Upper Cane — RHS 165B.

*Spines*.—Present. Spine density: Base: 6.5/cm$^2$ | Middle: 0/cm$^2$ | Tip: 1/cm$^2$. Spine shape: Acuminate. Spine length: 0.2 cm. Spine width: 0.05 cm. Spine apex descriptor: Acuminate. Spine color: RHS 164A.

*Reproductive bud shape*.—Ovately rounded.

*Reproductive bud length*.—0.38 cm.

*Reproductive bud diameter* (*base*).—0.26 cm.

*Reproductive bud diameter* (*tip*).—0.16 cm.

*Reproductive bud color*.—RHS 166B.

*Reproductive bud texture*.—Smooth.

*Winter hardiness*.—This cultivar is best adapted to the mild coastal conditions of USDA Hardiness Zone 9b (Watsonville, California). Since 2021, this cultivar has also been successfully tested under zero chill environments of central Mexico (Ciudad Guzman, Jalisco).

*Drought/heat tolerance*.—Pollen viability and fruit quality of raspberry generally begins to decline above 30° C. This is consistent with observations of 'HGF 1714'. Raspberries are generally not drought tolerant, and 'HFG 1714' has not been tested in unirrigated plots.

Leaves:

*Complete leaf*.—Leaf Shape: Even-Pinnate. Length: 18.0 cm. Width: 18.7 cm. Number of leaflets: 3 and 5.

*Terminal leaflet*.—Size Length: 10.3 cm. Width: 8.0 cm. Length/Width ratio: 1.3 cm. Leaf shape of apex: Acuminate. Leaf shape of base: Cordate. Leaf margin: Serrate. Leaf texture: Upper — Strongly rugose. Lower — Strongly rugose. Number of serrations per leaf: 96 serrations. Leaf shape of serrations: Flexuous. Leaf color: Upper Surface: RHS N137B. Lower Surface: RHS 191C. Leaf venation pattern: Palmate. Leaf venation color: Upper surface: RHS 144C. Lower surface: RHS 144D. Leaf pubescence density: N/A. Color of leaf pubescence: N/A. Shape of leaf in cross-section: Ovate. Number of leaflets/leaf: Primocane: 3 to 5 Floricane: 3. Interveinal blistering within leaf: Present. Leaf glossiness: Upper — Matte, no gloss. Lower — Matte, no gloss.

*Primocane leaves*.—Petiole length: 4.8 cm. Petiole diameter: 0.23 cm. Petiole Color: Upper: RHS 144C. Lower: RHS 144D. Petiole texture: Smooth with sparse spines. Stipule length: 1.0. Stipules per leaf: 2. Stipule Width: 0.013 cm. Stipule Color: Upper Surface: RHS 144D. Lower Surface: RHS 144C.

*Terminal leaflet*.—Shape: Ovate. Length: 12.8 cm. Width: 8.6 cm. Rachis length: 8.9 cm. Rachis diameter: 0.23 cm. Rachis texture: Upper — Smooth. Lower — Smooth with sparse spines. Rachis Color: Upper — RHS 145A. Lower — RHS 145A.

*Distal lateral leaflet*.—Shape: Ovate. Length: 10.4 cm. Width: 5.9 cm. Petiolule length: Sessile.

*Basal lateral leaflet*.—Shape: Ovate. Length: 11.7 cm. Width: 7.9 cm. Petiolule length: 0.75 cm. Petiolule diameter: 0.18 cm. Petiolule texture: Upper — Smooth. Lower — Smooth with sparse spines. Petiolule color: Upper — RHS 145A. Lower — RHS 145A.

*Floricane leaves*.—Petiole length: 5.65 cm. Petiole Diameter: 0.22 cm. Petiole Texture: Smooth with sparse spines. Petiole Color: Upper — RHS 145A. Lower — RHS 145A. Stipule length: 0.57 cm. Stipules per leaf: 2. Stipule Width: 0.013 cm. Stipule Color: Color Upper surface: RHS 144A. Lower surface: RHS 144A.

*Terminal leaflet*.—Shape: Ovate. Length: 12.8 cm. Width: 8.6 cm. Rachis length: 2.4 cm. Rachis diameter: 0.14 cm. Rachis texture: Smooth with sparse spines. Rachis Color: Upper — RHS 145A. Lower — RHS 145A.

*Distal lateral leaflet*.—N/A. Length: N/A. Width: N/A.

*Basal lateral leaflet*.—Shape: Ovate. Length: 11.7 cm. Width: 7.9 cm. Petiolule length: 0.21 cm. Petiolule diameter: 0.16 cm. Petiolule color: Upper — RHS 145A. Lower — RHS 145A.

Flowers:

*Time of flowering* (50% *of plants at first flower*).—Approximately 145 days after planting (on primocanes).

*Flower size*.—Length: 0.83 cm. Diameter: 0.83 cm.

*Fragrance*.—None.

*Peduncle*.—Length: 1.26 cm. Diameter: 0.05 cm. Color: RHS N144D. Pubescence: Not Present. Texture: Spiny.

*Perianth*.—Flowering trusses shape: Truncate.

*Petals*.—Color: Upper — RHS 155C | Lower — RHS 155C. Number per flower: 5 petals. Shape: Ovate. Length: 0.7 cm. Width: 0.3 cm. Apex descriptor: Rounded. Base Descriptor: Cuneate. Margin descriptor: Entire. Texture: Smooth with mild striations.

*Sepals*.—Quantity: 5-6. Length: 0.64 cm. Width: Base — 0.47 cm | Mid — 0.34 cm | Tip — 0.005 cm. Color: RHS 144D. Apex descriptor: Acuminate. Margin descriptor: Entire. Texture: Lightly pubescent.

*Pedicel*.—Color: RHS 144C. Length: 1.95 cm. Diameter: 0.15 cm.

Reproductive organs:

*Self-fertile*.—Yes, moderately self-fertile.

*Male*.—Stamen Number: 97. Filament Length: 0.38 cm. Diameter: 0.001 cm. Color: RHS 155A. Anther Length: 0.001 cm. Diameter: 0.002 cm. Color: RHS 165A. Pollen Color: RHS 197D. Amount: Moderate.

*Female*.—Style Length: 0.52 cm. Diameter: 0.004 cm. Color: RHS 157A. Stigma Length: 0.002 cm. Diameter: 0.003 cm. Color: RHS 159B. Ovary Length: 0.001. Diameter: 0.002. Color: RHS 144C.

Fruit:

*Predominant shape*.—Conical.

*Weight* (*g*).—7.2 g.

*Length*.—3.15 cm.

*Width*.—Base — 2.66 cm | Mid — 1.9 cm | Tip — 0.9 cm.

*Length/width ratio*.—1.18 cm.

*Receptacle*.—Length: 2 cm. Diameter: Base — 0.74 cm | Mid — 0.40 cm | Tip — 0.11 cm. Color: RHS 160D.

*Drupelet*.—Length: 0.60 cm. Diameter: 0.41 cm. Number: 133. Weight: 0.05 g.

*Fruit color*.—External: RHS 42B. Internal: RHS 44D.

*Firmness of skin*.—Very Firm.

*Firmness of flesh*.—Very Firm.

*Hollow center*.—Present.

*Fruiting lateral length*.—13 cm.

*Number of fruit per node*.—9.

*Time of ripening* (50% *of plants with first fruit*).—165 days after planting, on average.

*Time of fruiting*.—Mid-May to late June on floricanes; early September through early November on primocanes.

*Type of bearing*.—Remontant.

*Fruit yield*.—28,000 lb/a to 32,000 lb/a, on average.

*Average brix*.—9.39.

*Typical market use*.—Fresh.

*Keeping quality*.—Excellent, up to 20 days post-harvest.

*Shipping quality*.—Excellent.

Disease resistance: 'HFG 1714' shows mild susceptibility to yellow rust (*Phragmidium rubi-thunbergii*), a common fungal disease under commercial conditions. 'HFG 1714' has exhibited tolerance to the fungus-like oomycete *Phytophthora rubi-idaei* root rot and the fungus *Didymella applanata*.

What is claimed is:

1. A new and distinct cultivar of Raspberry plant named 'HFG 1714' as described and shown herein.

* * * * *